United States Patent
Estépar et al.

(10) Patent No.: US 8,644,574 B2
(45) Date of Patent: Feb. 4, 2014

(54) MEASUREMENT OF THIN-LAYERED STRUCTURES IN X-RAY COMPUTER TOMOGRAPHY

(75) Inventors: Raúl San José Estépar, Cambridge, MA (US); George R. Washko, West Roxbury, MA (US); Edwin K. Silverman, Brookline, MA (US); John J. Reilly, Pittsburgh, PA (US); Ron Kikinis, Chestnut Hill, MA (US); Carl-Fredrik Westin, Cambridge, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 1038 days.

(21) Appl. No.: 12/444,188

(22) PCT Filed: Oct. 3, 2007

(86) PCT No.: PCT/US2007/080259
§ 371 (c)(1),
(2), (4) Date: Jan. 11, 2010

(87) PCT Pub. No.: WO2008/042934
PCT Pub. Date: Apr. 10, 2008

(65) Prior Publication Data
US 2010/0172558 A1    Jul. 8, 2010

Related U.S. Application Data

(60) Provisional application No. 60/848,985, filed on Oct. 3, 2006.

(51) Int. Cl.
  *G06K 9/36* (2006.01)

(52) U.S. Cl.
  USPC .......................................... 382/131; 382/132

(58) Field of Classification Search
  USPC ................................................. 382/131, 132
  See application file for complete search history.

(56) References Cited

U.S. PATENT DOCUMENTS

| | | | |
|---|---|---|---|
| 6,173,084 B1 * | 1/2001 | Aach et al. ................... | 382/260 |
| 6,611,618 B1 * | 8/2003 | Peli .............................. | 382/154 |
| 6,956,975 B2 * | 10/2005 | Young .......................... | 382/263 |
| 7,003,071 B2 | 2/2006 | Nagaoka et al. | |
| 7,227,983 B1 * | 6/2007 | Christian et al. ............. | 382/141 |
| 7,711,148 B2 * | 5/2010 | Slabaugh et al. ............. | 382/103 |
| 7,991,185 B2 * | 8/2011 | Shi et al. ...................... | 382/100 |
| 8,200,022 B2 * | 6/2012 | Golan et al. .................. | 382/199 |
| 2004/0062345 A1 | 4/2004 | Kojima et al. | |

OTHER PUBLICATIONS

Raúl San José Estépar et al., "Accurate Airway Wall Estimation Using Phase Congruency," Ninth International Conference on Medical Image Computing and Computer-Assisted Intervention (MICCAI'06), pp. 125-134, Oct. 2006.*

(Continued)

*Primary Examiner* — Allen C. Ho
(74) *Attorney, Agent, or Firm* — Fish & Richardson P.C.

(57) ABSTRACT

A method for reconstructing an image includes receiving tomographic data representative of an image signal; deriving, from the image signal, a plurality of components; identifying a spatial location associated with maximum phase congruency of the components; incorporating, into an image, an edge at the spatial location; and providing an output representative of the image.

20 Claims, 8 Drawing Sheets

(56) References Cited

OTHER PUBLICATIONS

Shiying Hu et al., "Automatic Lung Segmentation for Accurate Quantitation of Volumetric X-Ray CT Images," IEEE Transactions on Medical Imaging, vol. 20, No. 6, pp. 490-498, Jun. 2001.*

Grégoire Malandain et al., "Topological Segmentation of Discrete Surfaces," International Journal of Computer Vision, vol. 10, Issue 2, pp. 183-197, Apr. 1993.*

M. C. Morrone and R. A. Owens, "Feature detection from local energy," Pattern Recognition Letters, vol. 6, Issue 5, pp. 303-313, 1987.*

Joseph M. Reinhardt et al., "Accurate Measurement of Intrahoracic Airways," IEEE Transactions on Medical Imaging, vol. 16, No. 6, pp. 820-827, Dec. 1997.*

Svetha Venkatesh and Robyn Owens, "On the classification of image features," Pattern Recognition Letters, vol. 11, pp. 339-349, May 1990.*

Estépar et al., "Accurate Airway Wall Estimation using Phase Congruency," Lecture Notes in Computer Science, Springer Berlin/Heidelberg, vol. 4191:125-134 (2006).

International Search Report for PCT/US2007/080259 dated Mar. 10, 2008.

* cited by examiner

MEASUREMENT OF THIN-LAYERED STRUCTURES IN X-RAY COMPUTER TOMOGRAPHY

RELATED APPLICATIONS

This application is a PCT application claiming the benefit of the priority date of U.S. Provisional Application No. 60/848,985, filed Oct. 3, 2006, the contents of which are incorporated herein by reference.

STATEMENT OF GOVERNMENT RIGHTS

This work disclosed herein was funded by NIH grants R01 HL 075478 and R01 HL 68926. The Federal government may have certain rights in the invention.

BACKGROUND

Computer tomography (CT) is a scanning technique that produces an image by measuring the absorption of X-ray energy by a structure of interest. The raw data generated from these measurements can be organized into an absorption map by means of the inverse Radon Transform. The result is the typical radiographic image used in many aspects of research and clinical care. While these images are often subjectively assessed by visual inspection, there is a growing need for more reproducible quantitative measurements within a region of interest. Examples of applications in which such needs exist include:

1. Measurements of airway wall thickness in the lungs. These measurements have been shown to correlate with clinical indices of such lung diseases as Chronic Obstructive Pulmonary Disease (COPD) and are being refined for use as biomarkers for monitoring disease progression.
2. Quantitative assessments of coronary artery narrowing for use as both a diagnostic measure of heart disease and as indices of disease progression.
3. Quantification of lung nodule size. It is estimated that 40% of people who smoke or used to smoke have lung nodules on their CT scans. Factors such as nodule size and rate of change in size are important prognostic pieces of data guiding therapy for possible lung cancer.
4. Quantitative assessments of the amount of cartilage in both normal and injured joints for both diagnostic purposes and therapeutic planning.
5. Assessment of material integrity in quality control processes and flaw detection. CT is sometimes used to detect internal structural problems in materials. The accuracy of the detection process depends in part on the accurate measurement of small defects and cracks.

The challenge when measuring fine structures is that the spatial resolution of the CT scanner imposes a lower limit on the size of a structure that can be accurately assessed. This limit is given by the Nyquist theorem, which states that the ability to quantitatively resolve structure size depends upon the scanner's point spread function (PSF). The scanner PSF is related to the reconstruction process that is done during the inverse Radon Transform. Traditionally, the PSF is modeled as a Gaussian function with a given variance. When the thickness of the structure is of the same order as the variance, the structure measurement is biased towards an overestimation of truth.

Additional factors that influence quantitative structural analysis include the algorithm used to reconstruct the image from the raw data, and the dose of radiation used to acquire the absorption map. Changes in either of these variables between CT scans can make anything more than subjective comparisons inaccurate. These considerations significantly impact longitudinal research based on clinical studies (i.e. following the change in size of a lung nodule when the images were obtained at different hospitals or different scanner settings) and large multicenter studies, where each site may be using a different scanning protocol for image acquisition.

SUMMARY

The invention features an application of the phase congruency principle to implement a model-free method that is independent of scanning PSF for locating edges in connection with the measurement of thin-layered and fine structures in CT ("computerized-tomography") images.

In one aspect, the invention features a method for reconstructing an image by receiving tomographic data representative of an image signal; deriving, from the image signal, a plurality of components; identifying a spatial location associated with maximum phase congruency of the components; incorporating, into an image, an edge at the spatial location; and providing an output representative of the image.

Practices of the invention include those in which deriving a plurality of components from the image signal includes passing the image signal through each of a plurality of filters; whereby the output of each such filter results in one of the plurality of components. Exemplary filters include quadrature pair filters, such as log-Gabor filter.

Other practices include those in which identifying a spatial location associated with a maximum phase congruency includes for each of a plurality of locations, determining a consistency of local phase among the components; and identifying a spatial location showing the maximum consistency to be the location associated with maximum phase congruency.

Additional practices include those in which deriving a plurality of components includes defining a plurality of kernels, each of which corresponds to one of the components. Among these practices are those in which identifying a spatial location includes operating on the image signal with each of the kernels, thereby generating a corresponding plurality of responses, and estimating a common crossing point of the responses. Exemplary kernels include zero-phase kernels.

In another aspect, the invention features a manufacture that includes a computer-readable medium having encoded thereon software for reconstructing an image. The software includes instructions for receiving tomographic data representative of an image signal; deriving, from the image signal, a plurality of components; identifying a spatial location associated with maximum phase congruency of the components; incorporating, into an image, an edge at the spatial location; and providing an output representative of the reconstructed image.

Additional embodiments of the manufacture include those having instructions for carrying out one or more of the foregoing methods.

Another aspect of the invention features a system for reconstructing an image on the basis of tomographic data representative of an image signal. Such a system includes means for deriving, from the image signal, a plurality of components; a phase-congruency detector for providing, on the basis of the components, a spatial location associated with maximum phase congruency of the components; an image-enhancement unit in data communication with the phase-congruency detector, the image-enhancement unit being configured to incorporate, into an image, an edge at the spatial location; and an output device in data communication with the image-enhancement unit for providing output representative of the reconstructed image.

Embodiments of the system include those in which the means for deriving an image signal includes a plurality of filters, the output of each filter providing one of the components. Exemplary filters include quadrature pair filters, such as log-Gabor filters.

Other embodiments of the system include those in which the means for deriving an image includes a plurality of kernels, each of which corresponds to one of the components.

These and other features of the invention will be further apparent from the following detailed description and the accompanying claims, in which:

DETAILED DESCRIPTION

Under phase congruency, the location of relevant features, i.e. edges or lines, is given by those locations at which local phase exhibits maximal coherency. Phase congruency, which is present at the scanner level when reconstructing the data with different reconstruction kernels, is used herein for the measurement of thin-layered structures. Because methods relying on phase congruency for edge detection and definition are model free, the reconstruction algorithm and image noise (which is inversely influenced by radiation dose) have a significantly smaller impact on image quantification than current techniques.

The detection of small and thin-layered structures through phase congruency can be done by either:

1. carrying out multiple kernel reconstruction, or
2. carrying out a single kernel reconstruction.

Figure 1:
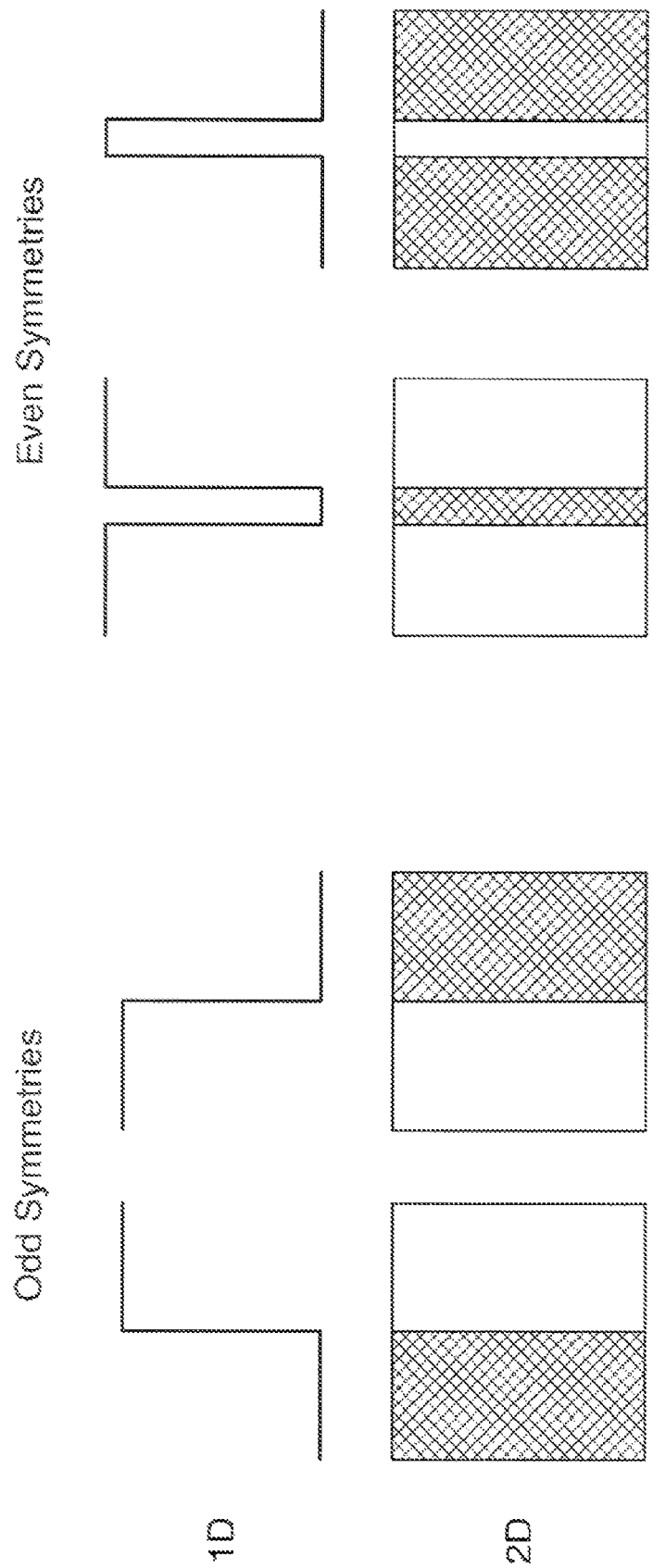
FIG. 1 shows the decomposition of a signal into odd and even symmetries.

Conceptually, an image can be locally decomposed into a linear combination of a reduced set of symmetries, namely, edges (which are referred to as "odd" symmetries) and lines (which are referred to as "even" symmetries). FIG. 1 illustrates the two types of symmetries that can be locally found in a one-dimensional signal and a two-dimensional signal (i.e. an image). Image symmetries, such as those shown in FIG. 1, are often perceived as locations where the Fourier components of the image are maximally in phase. This in-phase behavior, referred to herein as phase congruency, can be used as a feature descriptor.

Figure 2A:
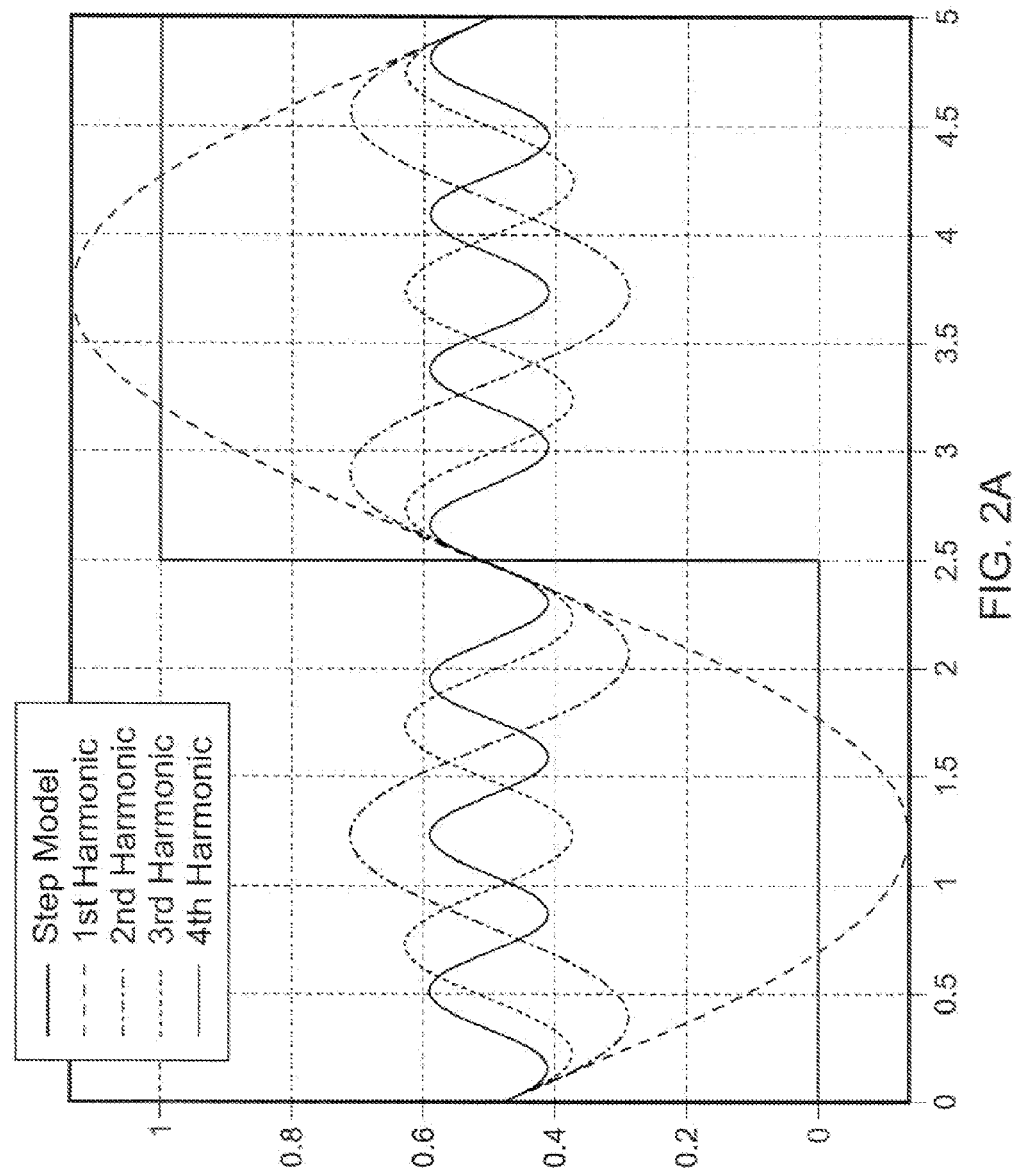
FIG. 2A shows the first four harmonies of a Fourier series approximation of a step function.
Figure 2B:
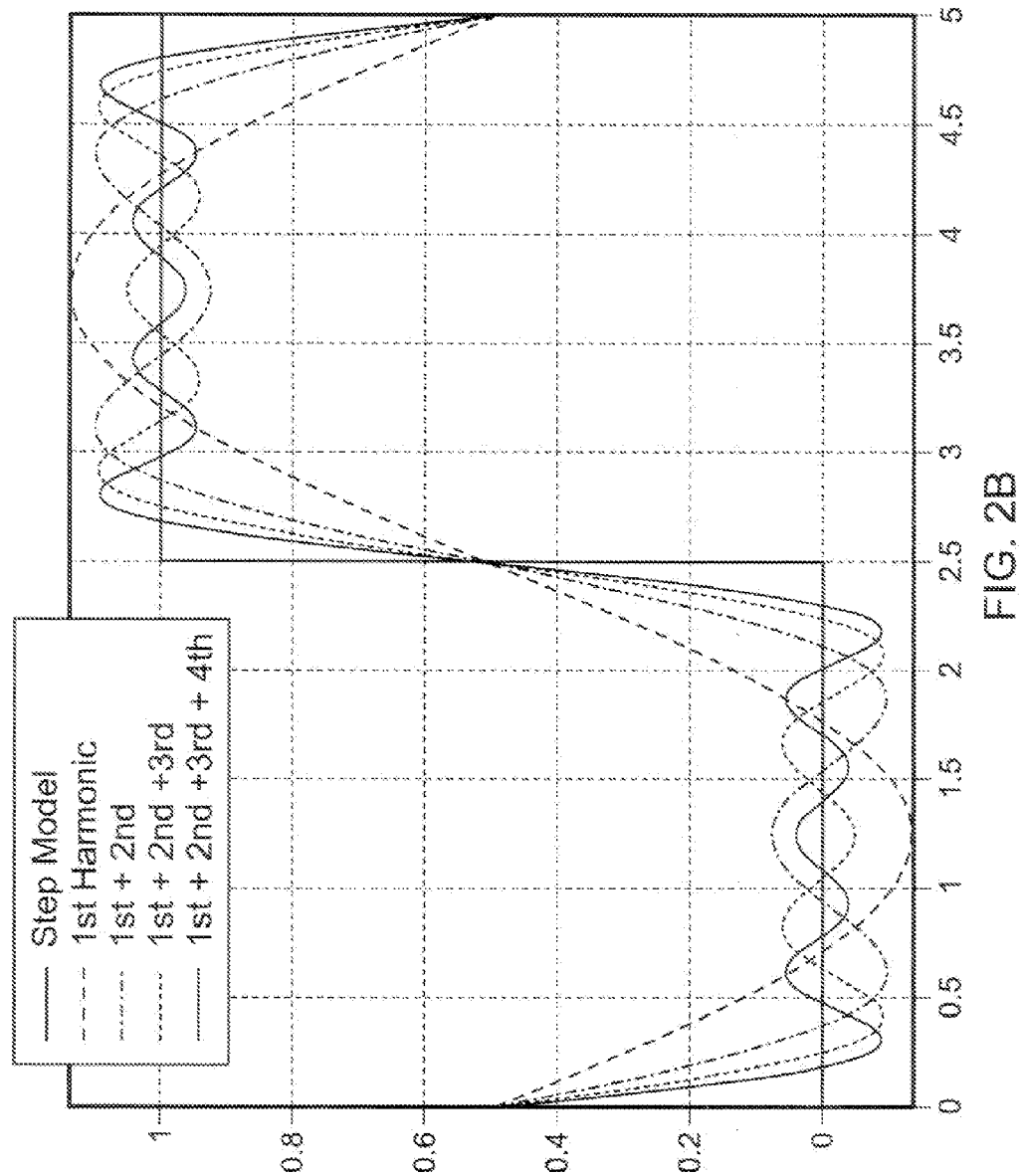
FIG. 2B shows the approximations resulting from summation of different numbers of harmonics.

A signal associated with an edge, or boundary, can be locally approximated by a step function. Such a signal can arise as a CT signal, an MRI signal, or any other imaging signal. The first four harmonics of a Fourier series approximation of the step function, shown in FIG. 2A, are in-phase only at the step transition. This property is useful for identifying local symmetries. FIG. 2B shows how the Fourier series more closely approximates the step function as the number of terms in the Fourier series increases.

Although the four approximations differ significantly on either side of the step function's discontinuity, they nevertheless share a crossing point at the step discontinuity. This shared crossing point arises from in-phase behavior, i.e. maximal phase congruency of the individual harmonics.

Phase congruency can be used to characterize the location of transitions, such as those that mark the boundary of a lumen, including the boundary of an airway, a blood vessel, a digestive organ, cell walls, and the like. Phase congruency exploits signal properties that are preserved even when the signal undergoes smoothing, such as smoothing introduced by the scanner's point spread function. Among the ways of measuring phase congruency are those that rely on multiple reconstruction kernels, and those that rely on computational methods using a single reconstruction kernel.

Multiple Kernel Reconstructions

The reconstruction kernel is a parameter of the reconstruction process that governs the averaging of neighboring samples in the projection space (Radon space) prior to back-projection to compute the final intensity of each pixel location. The reconstruction kernel thus directly affects the spatial frequency characteristics of the reconstructed image, which in turn affects how smooth or sharp the image appears. The overall behavior of the point-spread function can thus be changed by modifying the reconstruction kernel.

Figure 3A:
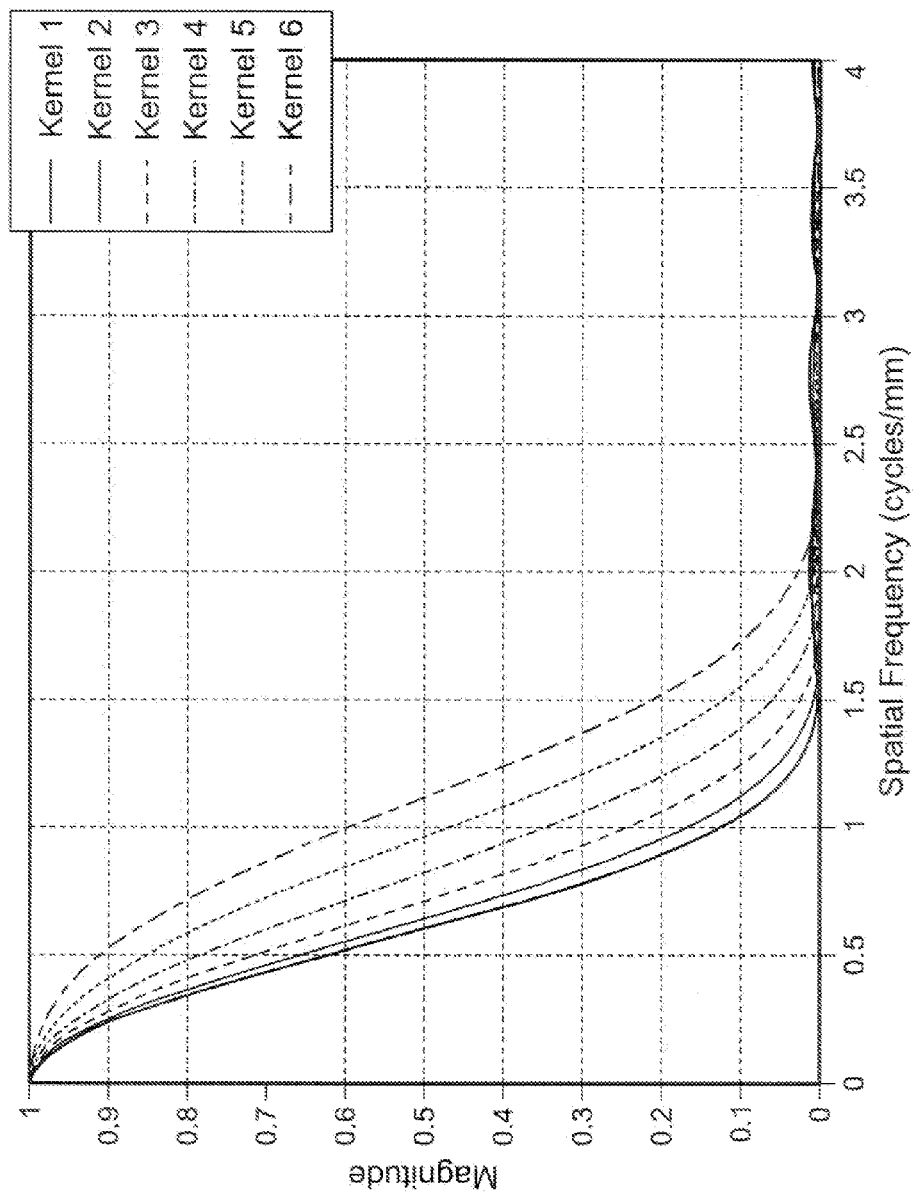
FIG. 3A shows spatial frequency responses for six synthetic point spread functions simulating six different kernels.
Figure 3B:
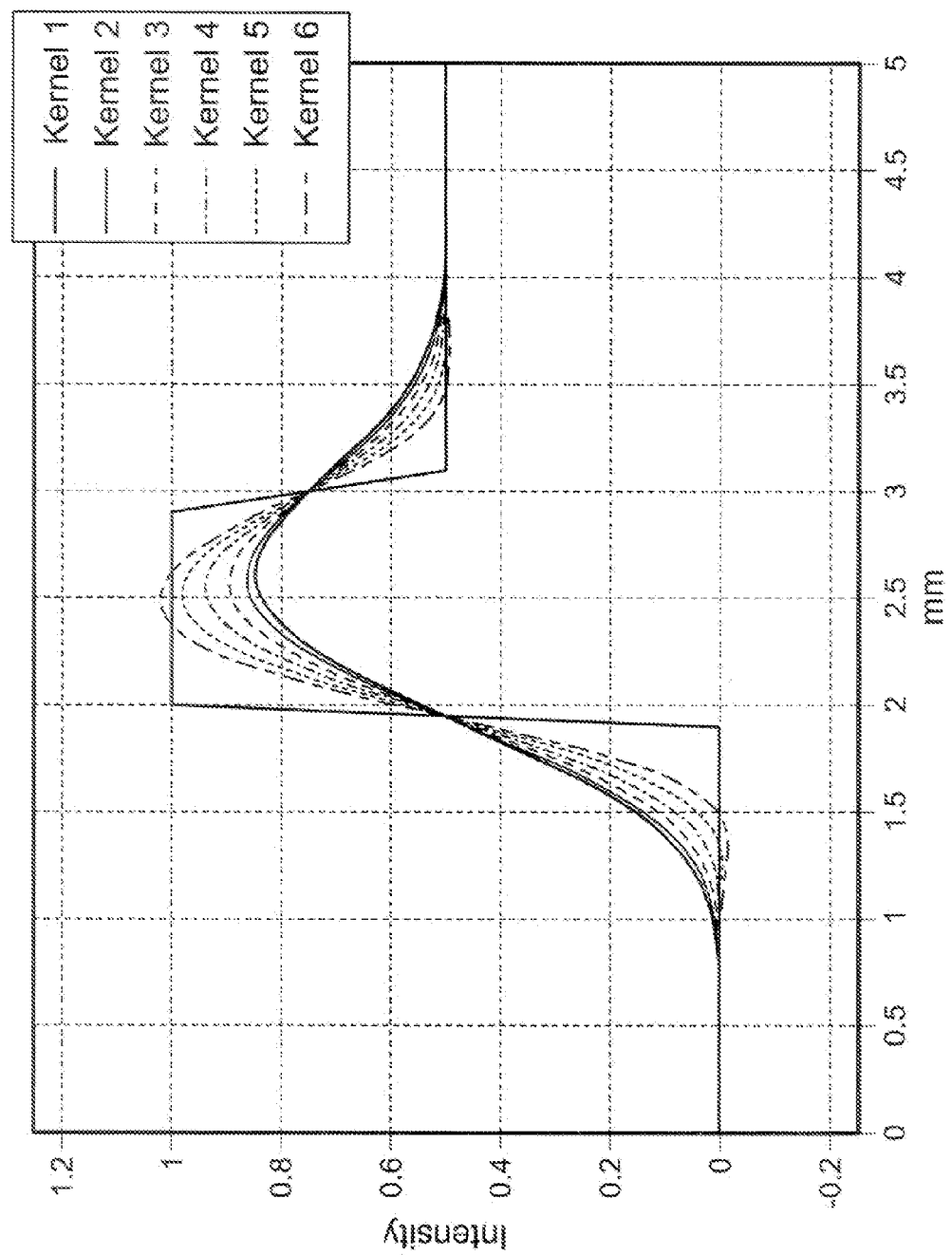
FIG. 3B shows six CT intensity responses corresponding to the point spread functions of FIG. 3A.

FIG. 3A shows the frequency responses associated with six synthetically generated point-spread functions, each of which corresponds to a kernel. The kernels yielding the widest spatial frequency bandwidth are those that yield the highest resolution. The responses of an ideal airway for each of the reconstruction kernels of FIG. 3A are shown in FIG. 3B. The common crossing point of the six responses indicates a point of maximal phase congruency, and therefore provides an estimate of airway wall location.

The location of the common crossing point can be estimated by obtaining the median intersection point for all possible pairs of kernels. In particular, given K kernels, the number of pair combinations is $$M = \frac{K!}{2(K-2)!}.$$

The inner and outer wall locations are then given by $$\rho_{ilo} = \text{median}\left(\bigcup_{i=1}^{M} \text{Inter}_{ilo}\{V(i)\}\right)$$

where V is the set of all pair combinations, $V(i)$ is the $i^{th}$ pair of the set, and $\text{Inter}_i$ and $\text{Inter}_o$ are the intersection operators that compute the intersection points between two kernel profiles for the inner and outer wall respectively.

The use of intersection operators and the median function represent one of many ways to estimate the location of an edge. For example, one can also evaluate a quantity that depends on an average or weighted average of kernel pairs.

A particularly useful kernel for estimating phase congruency is one that avoids introducing shifts in the reconstructed signal. Such kernels, often called zero-phase kernels, avoid distortion that would otherwise undermine an accurate measurement of phase congruency.

EXPERIMENTS

Figure 4:
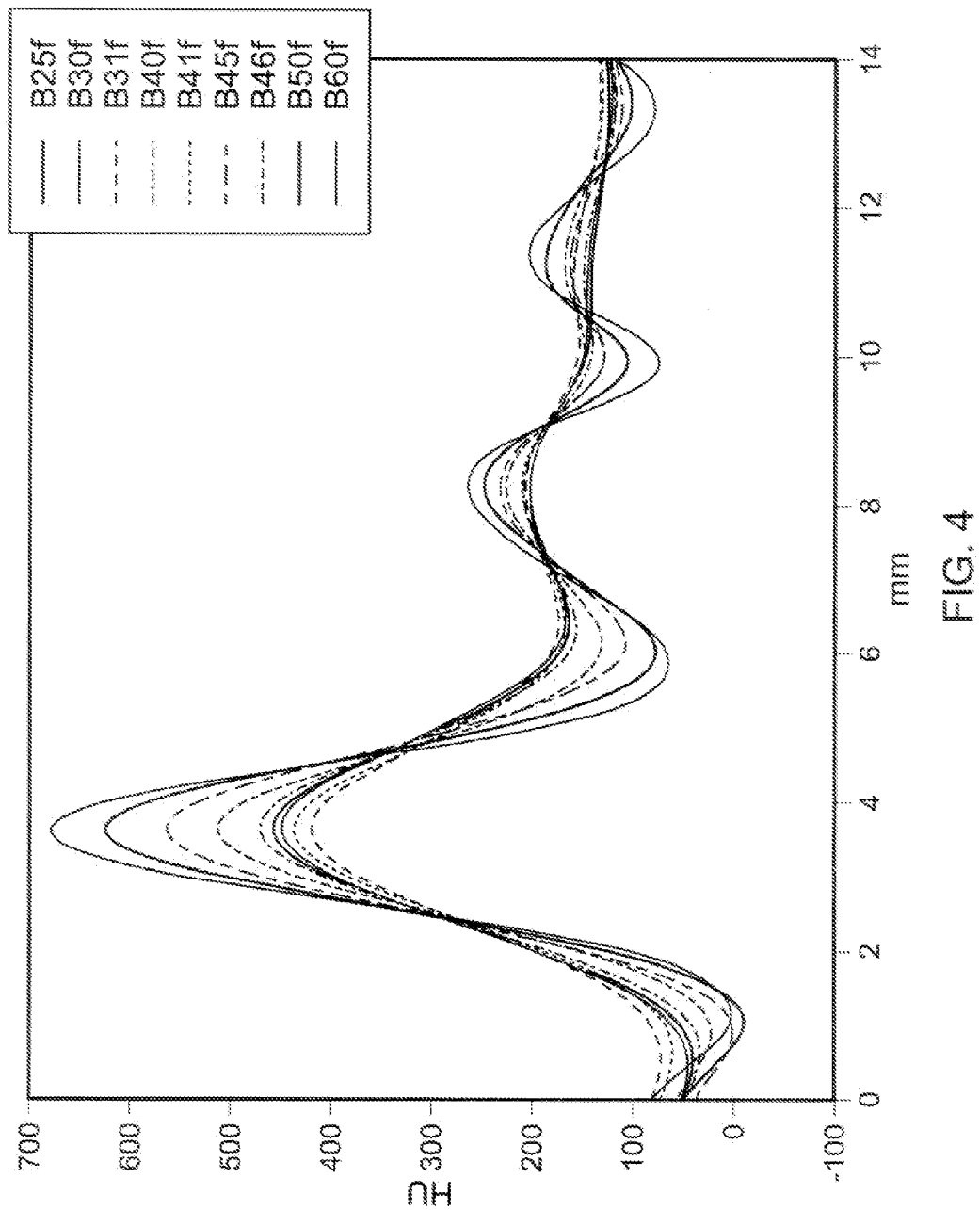
FIG. 4 shows intensity profiles along the radial direction in an airway.

The common crossing point across kernels was identified in in-vivo scans. FIG. 4, which shows the presence of maximal phase congruency for the reconstruction of an airway with nine different kernels, was obtained by scanning a tubular structure on a Siemens scanner and reformatting with nine different reconstruction kernels provided by the manufacturer. Each kernel was associated with a different point-spread function. Geographically identical intensity profiles cast from the interior of the tubular structure to the exterior in each of the reconstructed images were selected and superimposed graphically. As shown in FIG. 4, the different intensity profiles showed a crossing point. This crossing point corresponded to the location of maximum phase congruency, and therefore the edge or boundary of the structure of interest. Therefore, this "kernel crossing" method could be used for edge or feature detection. In particular, the intersection of two or more intensity profiles obtained from different reconstruction algorithms provided an estimate of edge location.

Features on an image are often perceived at those locations in which the Fourier components of the local signal are maximally in phase. These perceived features are associated with changes of intensity that arise from the presence of maximal phase congruency. These sites correspond to the sites at which intensity-profiles generated with different reconstruction kernels intersect.

Single Kernel Reconstruction

While the intersection of intensity profiles from different reconstruction kernels designates an image feature or edge, determination of these common points can also be made from a single intensity profile. This can be achieved by algorithmically estimating additional intensity profiles using the local phase.

In another embodiment, a measure of phase congruency from a single reconstruction kernel can be estimated by the local phase across different scales. In this embodiment, a filter bank decomposes an image into different sub-bands, each of which provides a measurement of the local phase of the image signal for a given scale. The consistency of the local phase across scales is then used as an indicator of phase congruency.

Local phase, which is the spatial counterpart of Fourier phase, is defined from the analytic signal corresponding to the real image signal. The analytic signal of a one-dimensional real signal f(x) is a complex-valued signal whose real part is the signal itself, and whose imaginary part is proportional to the Hilbert transform of the real signal:

$$f_A(x)=f(x)-iH\{f(x)\}=E(x)e^{i\phi(x)}$$

where $E(x)$ is the local energy of the signal and $\phi(x)$ is the local phase. The Hilbert transform operator, $H\{\ \}$, dephases all the frequency components by $-\pi/2$.

The analytic signal can be viewed as a complex number in the complex plane, the magnitude of which corresponds to the local energy; and the argument (i.e., the angle measured from the positive real axis) of which corresponds to the local phase.

The analytic signal thus provides a way to locally decompose the image signal into two orthogonal components: the local energy and the local phase.

As discussed above, an image signal can be locally decomposed into two basic symmetries: edges and lines. The local energy carries information about the strength of those symmetries regardless of their type. On the other hand, the local phase carries information about the type of symmetry regardless of the strength of that symmetry. Therefore, a weak edge and a very strong edge would have substantially the same local phase, because they are both edges. Similarly, a weak edge and a weak line would have substantially the same local energy because both are weak symmetries.

The analytic signal is well-defined for signals that are well localized in the frequency domain. For a signal with a wide frequency spectrum, it is useful to carry out a frequency localization before computing local phase. The analytic signal is well-defined for any bandpass version of the original signal. As a result, it is possible to achieve different measurements of the local phase for different bands, i.e. different scales. The analytic signal for a given sub-band is defined as $$f_{A_n}(x)=h_n(x)*f(x)+iH\{h_n(x)\}*f(x)=E_n(x)e^{i\phi_n(x)}$$

where $h_n$ and $H\{h_n\}$ form a quadrature pair (or a quadrature filter), with $h_n$ representing the band-pass filter corresponding to scale n. Among the suitable quadrature pairs are those from the log-Gabor filter family. However, any other quadrature pair can be used. Examples of other quadrature pairs include those from the Poisson family and those from the Differential Gaussian family.

A log-Gabor filter pair is defined in the Fourier domain as $$G(\omega) = e^{-\frac{log^2\left(\frac{\omega}{\omega_0}\right)}{2log^2\left(\frac{\kappa}{\omega_0}\right)}}$$

where $\omega_0$ is the center frequency of the filter, and $\kappa/\omega_0$ is a constant factor that defines the filter bandwidth. Each band-pass filter $h_n$, and its respective Hilbert transform $H\{h_n\}$ is then obtained as the real and imaginary parts of the inverse Fourier transform of the log-Gabor filter pair G respectively.

The individual filters of the filter bank each have a center frequency and a filter bandwidth. In one embodiment, the center frequency is a multiple of a base frequency. Such filter banks offer a designer three degrees of freedom: base frequency, multiplication factor, and filter bandwidth. Based on the definition of analytic signal, phase congruency, $\Psi$, is a normalized measure of local phase invariance across scales (modulated by a cosine function). In terms of the local phase, the phase congruency function is defined as $$\Psi(x) = \frac{\sum_{n=1}^{N} E_n(x)\cos(\phi_n(x) - \bar{\phi}(x))}{\sum_n E_n(x)}$$

where $\phi_n(x)$ is the local phase for scale n, $\bar{\phi}(x)$ is the average local phase, and N is the number of scales used in the analysis. The phase congruency function is also proportional to the local energy and can be calculated from the analytic signal components as $$\Psi(x) = \frac{\sqrt{\left(\sum_{n=1}^{N} \text{Re}\{f_{A_n}\}\right)^2 + \left(\sum_{n=1}^{N} \text{Im}\{f_{A_n}\}\right)^2}}{\sum_{n=1}^{N} \|f_{A_n}\|}$$

The phase congruency function is a smooth function having local maxima at those locations in which the local phase is consistent across scales, and values that vary from a maximum of 1 (indicating a very significant symmetry) down to 0 (indicating no significance).

Figure 5:
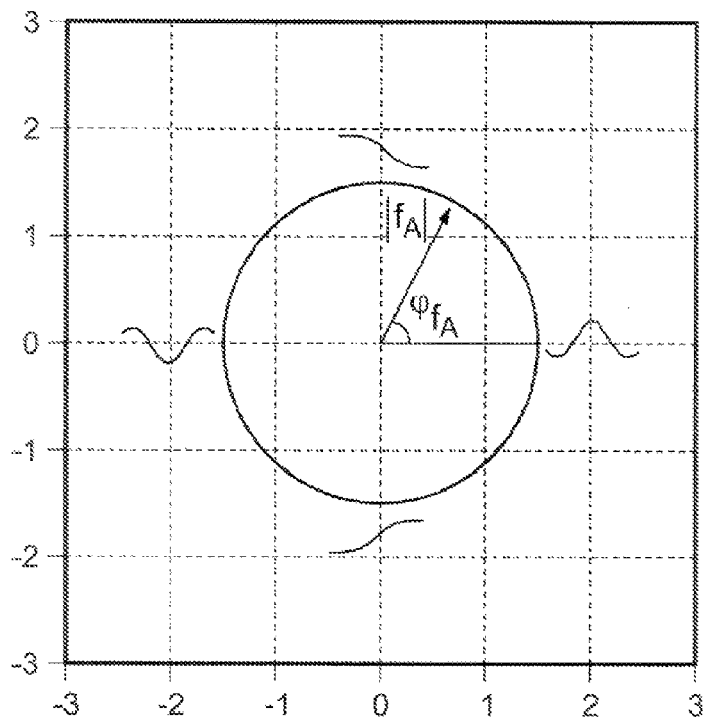
FIG. 5 is a local phase diagram for a one-dimensional signal annotated at selected angles to illustrate local structures that originate phase behavior.

It is useful to distinguish between those locations at which the local maxima in phase congruency are due to the inner wall edge, and those locations at which the local maxima are due to the outer wall edge. This distinction can be identified by using the "type-of-symmetry" encoding properties of the local phase. A suitable measure for phase congruency is feature dependent phase congruency, $\Psi_\theta$, which is given by $$\Psi_\theta(x) = \Psi(x) \max(\cos(\bar{\phi}(x) - \theta), 0)$$

where $\theta$ depends on the feature type to which the phase congruency measure is to be tuned. Based on the meaning of the local phase depicted in FIG. 5, for a dark-to-bright edge, $\theta = \pi/2$, and for a bright-to-dark edge, $\theta = 3\pi/2$. Therefore, the inner wall would be given by the location that maximizes $\Psi_{\pi/2}(x)$, and the outer wall would be given by the location that maximizes $\Psi_{3\pi/2}(x)$. The inner and outer wall locations are then respectively defined as $$\rho_i = \arg\max \Phi_{\pi/2}(x), \; \rho_o = \arg\max \Phi_{3\pi/2}(x)$$

The foregoing embodiment of an edge-detection method can be decomposed into the following stages:
1. Filter the input intensity of a CT profile with a bank of quadrature filters, each filter being tuned at a different frequency and having a given bandwidth.
2. From the response of each filter, compute the standard phase congruency measure
3. Compute the feature-dependent phase congruency for $\theta = \pi/2$ and $\theta = 3\pi/2$ to yield two new signals, the maxima of which correspond to the locations of the boundaries of a thin-layered structure.
4. Detect the boundaries by finding the maxima of the preceding two signals.
5. On the basis of the detected boundaries, calculate the thickness of the structure.

Figure 6:
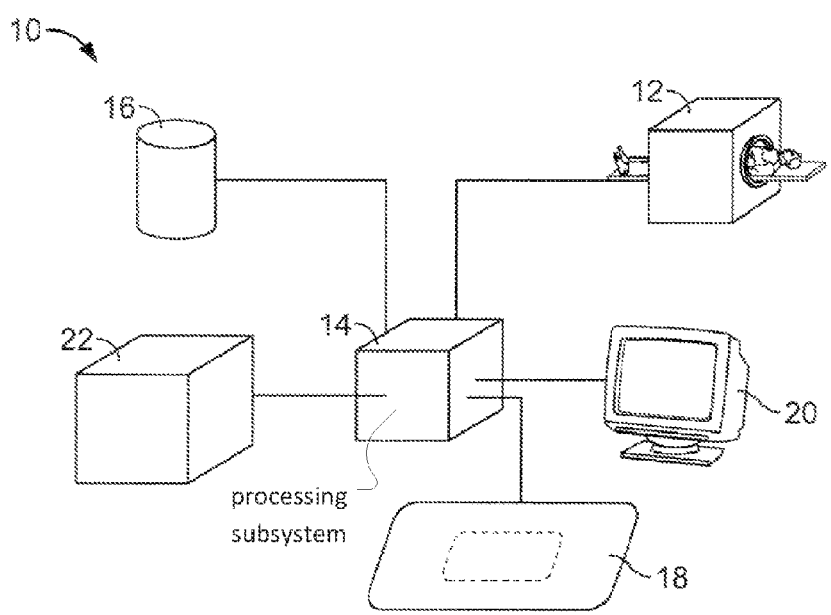
FIG. 6 is a system for carrying out the edge-detection method.

FIG. 6 shows a system 10 for carrying out the phase congruency imaging method described herein. The system receives CT data representative of an image signal from a medical imaging device, such as a CT scanner 12.

A processing subsystem 14 receives the CT data from the scanner 12 and executes instructions stored on a manufacture that includes a computer-readable medium 16. Examples of computer-readable media 16 include memory, both volatile and non-volatile, disks, including magnetic disks and CD-ROM disks, tapes, or any combination thereof. The computer-readable medium 16 need not be local to the processing subsystem 14, but can instead communicate with the processing subsystem 14 through a network.

In response to instructions provided by a user using an input device 18, such as a keyboard or mouse, the processing subsystem 14 causes these instructions to be executed. In so doing, the instructions carry out the phase congruency methods described herein.

The processing subsystem 14 provides tangible output to a display device 20 and/or to a printer 22. This output is relied upon by a clinician in assessing anatomical structures within a patient. As a result, the system 10 has utility to, among others, a clinician or doctor who uses the anatomical structures revealed by the method to make recommendations in connection with the patient's health care.

Figure 7:
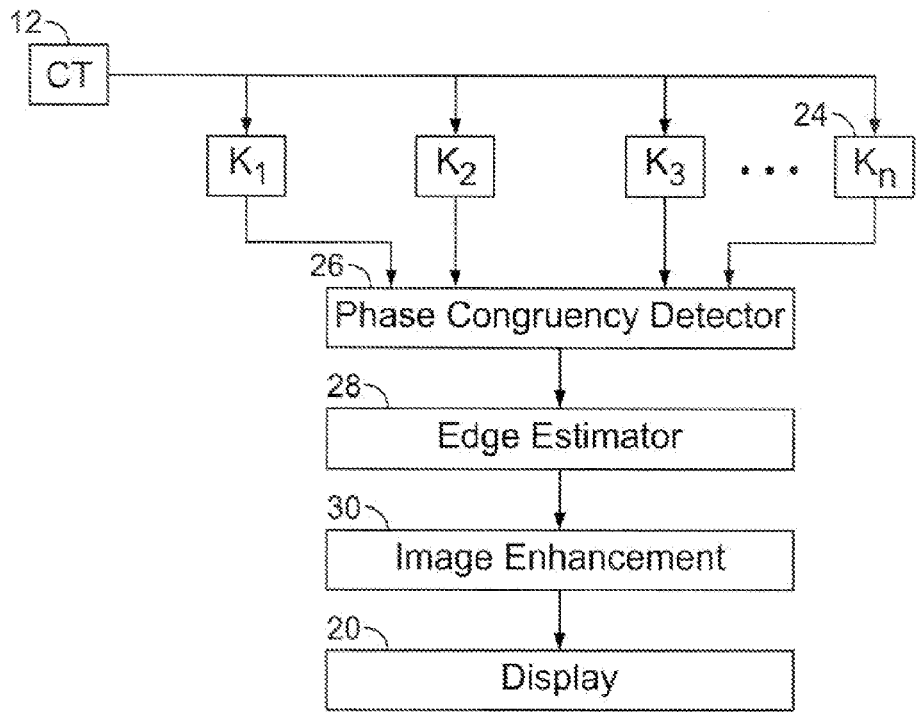
FIG. 7 shows the architecture of a computer-implemented system for carrying out the edge-detection method using multiple kernels.

In one embodiment, shown in FIG. 7, the system 10 generates a plurality of synthetic kernels 24, $K_1, K_2, K_3, \ldots K_n$. These kernels 24 are combined with the CT data from the CT scanner 12. The result of such combination is a response of the image signal to each kernel 24. These differing responses are provided to a phase congruency determination unit 26, which identifies the spatial locations at which phase congruency is maximized. The phase congruency determination unit 26 then provides an output to an edge estimator 28. On the basis of data provided by phase congruency determination unit 26, the edge estimator 28 estimates a likely location of an edge using the methods described above. The edge estimator 28 output is then provided to an image-enhancement module 30, which merges data representative of edges with tomographic data from the CT scanner 12. The resulting data is then rendered either by a display 20 or a printer 22 into human-readable form that can be used as a basis for medical decision-making.

Figure 8:
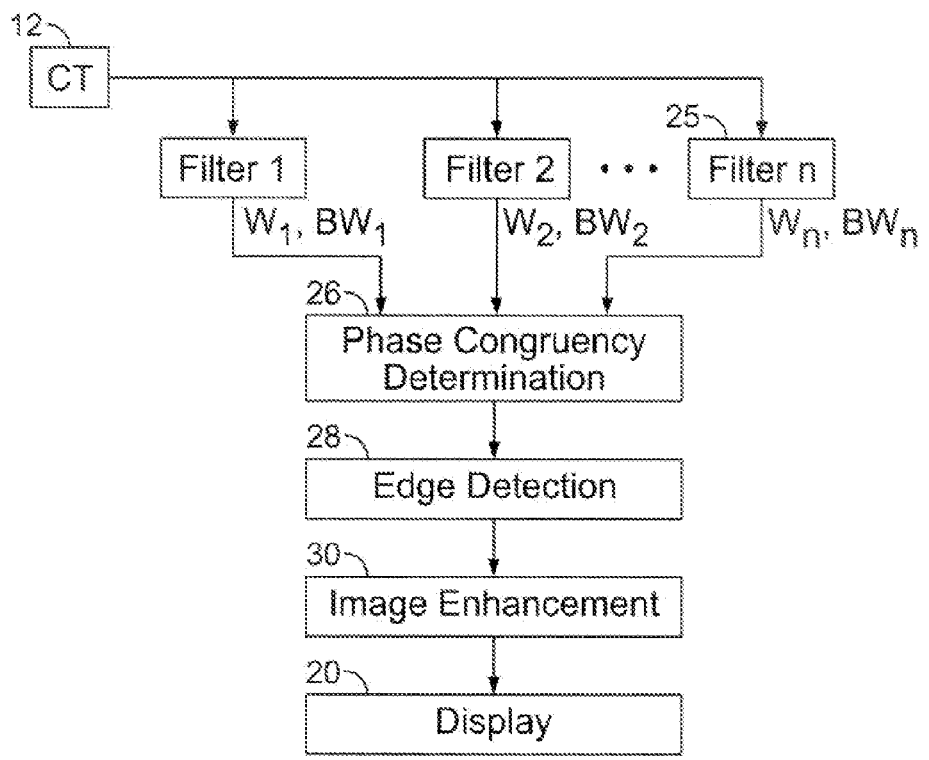
FIG. 8 shows the architecture of a computer-implemented system for carrying out the edge-detection method using a single kernel.

In another embodiment, shown in FIG. 8, the system includes a plurality of band-pass filters 25, each of which has a particular center frequency ($W_1, W_2, \ldots W_n$) and a bandwidth ($BW_1, BW_2, \ldots BW_n$). The outputs of these band-pass filters 25 play a role similar to that played by the synthetic kernels 24 described above in connection with FIG. 7. The remaining structures in FIG. 8 are similar to those described above in connection with FIG. 7.

This method can be implemented by software applications customized for the structures under consideration. Manufacturers of imaging equipment usually offer their customers additional software packages for the analysis of images provided by the scanner. The model-free method of image-based structural definition and quantification is less subject to image noise than currently available techniques. This means that for structural analysis and quantification, the method of phase congruency for edge detection may provide useful information with a radiation dose lower than that currently required. This reduction in radiation improves subject safety and reduces the risk of certain cancers.

Imaging devices are instrumental in the in-vivo characterization of morphological changes of the anatomy due to disease processes or aging. The advantage of such tools is that serial investigations can be made in a minimally invasive fashion with minimal subject discomfort. Because of this, CT scanning has been proposed to fill multiple needs, including providing a biomarker for clinical and research-based investigations, and as a diagnostic tool to assess the presence and burden of disease.

An example of a commercial application of such a tool is in the area of drug discovery to hasten the production cycle for a given drug. One result of this is that imaging, and more specifically, quantitative assessments of a disease characteristic, has become one of the main tools for identifying a disease-associated biomarker. This measure has to be unbiased, reliable and reproducible. Methods that enable such measurements are therefore in demand from the pharmaceutical industry because of their utility in discovery and clinical trials of new drugs.

Additionally, disease diagnosis is more commonly based on measurements obtained empirically from imaging devices. Radiologists often rely on a well-defined but subjective scoring system to quantify the burden of a disease. Examples of this are found in the assessments of coronary plaques found in heart disease and airway wall thickening associated with certain lung diseases. Finally, clinical decisions are often based upon radiographic findings. For example, size and growth rate of a lung nodule can be used to decide between surgical resection and serial radiographic observation. Unfortunately, such decisions are often based upon visual measurements that are subject to intra and inter-expert variation. Clinicians are therefore likely to find uses for software based on the methods disclosed herein.

Having described the invention, and a preferred embodiment thereof, what we claim is new and secured by Letters Patent is:

1. A computer-implemented method for reconstructing an image, the method comprising:
   causing an electronic digital computer to receive tomographic data representative of an image signal;
   causing the electronic digital computer to derive, from the image signal, a plurality of components;
   causing the electronic digital computer to identify a spatial location associated with maximum phase congruency of the plurality of components;
   causing the electronic digital computer to incorporate, into an image, an edge at the spatial location; and
   causing the electronic digital computer to provide an output representative of the image.

2. The method of claim 1, wherein causing the electronic digital computer to derive a plurality of components from the image signal comprises:
   causing the electronic digital computer to pass the image signal through each of a plurality of filters;
   whereby the output of each such filter results in one of the plurality of components.

3. The method of claim 2, wherein causing the electronic digital computer to identify a spatial location associated with a maximum phase congruency comprises:
   for each of a plurality of locations, causing the electronic digital computer to determine a consistency of local phase among the plurality of components; and
   causing the electronic digital computer to identify a spatial location showing the maximum consistency to be the location associated with maximum phase congruency.

4. The method of claim 2, further comprising selecting the filters to be quadrature pair filters.

5. The method of claim 1, wherein causing the electronic digital computer to derive a plurality of components comprises causing the electronic digital computer to define a plurality of kernels, each of which corresponds to one of the plurality of components.

6. The method of claim 5, wherein causing the electronic digital computer to identify a spatial location comprises causing the electronic digital computer to operate on the image signal with each of the kernels, thereby generating a corresponding plurality of responses, and estimating a common crossing point of the responses.

7. The method of claim 5, further comprising selecting the kernels to be zero-phase kernels.

8. A manufacture comprising a non-transitory computer-readable medium having encoded thereon software for reconstructing an image, the software including instructions for:
   receiving tomographic data representative of an image signal;
   deriving, from the image signal, a plurality of components;
   identifying a spatial location associated with maximum phase congruency of the plurality of components;
   incorporating, into an image, an edge at the spatial location; and
   providing an output representative of the image.

9. The manufacture of claim 8, wherein the instructions for deriving a plurality of components from the image signal include instructions for:
   passing the image signal through each of a plurality of filters;
   whereby an output of each such filter results in one of the plurality of components.

10. The manufacture of claim 9, wherein the instructions for identifying a spatial location associated with a maximum phase congruency include instructions for:
    for each of a plurality of locations, determining a consistency of local phase among the plurality of components; and
    identifying a spatial location showing the maximum consistency to be the location associated with maximum phase congruency.

11. The manufacture of claim 9, wherein the software further includes instructions for selecting the filters to be log-Gabor filters.

12. The manufacture of claim 8, wherein the instructions for deriving a plurality of components include instructions for defining a plurality of kernels, each of which corresponds to one of the plurality of components.

13. The manufacture of claim 12, wherein the instructions for identifying a spatial location include instructions for operating on the image signal with each of the kernels, thereby generating a corresponding plurality of responses, and estimating a common crossing point of the responses.

14. The manufacture of claim 12, wherein the instructions further include selecting the kernels to be zero-phase kernels.

15. An electronic data processing system for reconstructing an image on the basis of tomographic data representative of an image signal, the system comprising:
    an electronic processor for executing instructions, and a memory in data communication with the electronic processor, the memory having recorded thereon instructions that, when executed by the electronic processor, cause the establishment of means for deriving, from the image signal, a plurality of components;
    a phase-congruency detector for providing, on the basis of the plurality of components, a spatial location associated with maximum phase congruency of the plurality of components, and
    an image-enhancement unit in data communication with the phase-congruency detector, the image-enhancement unit being configured to incorporate, into an image, an edge at the spatial location; and
    an output device in data communication with the image-enhancement unit for providing output representative of the image.

16. The system of claim 15, wherein the means for deriving an image signal comprises a plurality of filters, the output of each filter providing one of the plurality of components.

17. The system of claim 16, wherein the plurality of filters comprises quadrature pair filters.

18. The system of claim 16, wherein the plurality of filters comprises log-Gabor filters.

19. The system of claim 15, wherein the means for deriving an image comprises a plurality of kernels, each of which corresponds to one of the components.

20. The system of claim 15, further comprising a CT scanner for providing the tomographic data.

* * * * *

UNITED STATES PATENT AND TRADEMARK OFFICE
CERTIFICATE OF CORRECTION

PATENT NO. : 8,644,574 B2
APPLICATION NO. : 12/444188
DATED : February 4, 2014
INVENTOR(S) : Estepar et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1319 days.

Signed and Sealed this
Twenty-first Day of July, 2015

Michelle K. Lee
*Director of the United States Patent and Trademark Office*